US006790972B1

United States Patent
Nguyen Ngoc et al.

(10) Patent No.: US 6,790,972 B1
(45) Date of Patent: Sep. 14, 2004

(54) POLYMERISATION CATALYSTS

(75) Inventors: Hanh Nguyen Ngoc, Thanh Pho Ho Chiminh (VN); Heinz Gornitzka, Pompertuzat (FR); Blanca Martin-Vaca, Toulouse (FR); Didier Bourissou, Plaisance Du Touch (FR); Guy Bertrand, Riverside, CA (US); Jean-Bernard Cazaux, Aramon (FR)

(73) Assignees: Societe de Conseils de Recherches et d'Applications Scientifiques (S.C.R.A.S.) (FR); Centre National de la Recherche Scientifique (C.N.R.S.) (FR)

( * ) Notice: Subject to any disclaimer, the term of this patent is extended or adjusted under 35 U.S.C. 154(b) by 289 days.

(21) Appl. No.: 10/019,167
(22) PCT Filed: Jun. 23, 2000
(86) PCT No.: PCT/FR00/01753
§ 371 (c)(1),
(2), (4) Date: Dec. 20, 2001
(87) PCT Pub. No.: WO01/00628
PCT Pub. Date: Jan. 4, 2001

(30) Foreign Application Priority Data

Jun. 25, 1999 (FR) .......................................... 99 401585

(51) Int. Cl.[7] .............................. C07F 3/06; B01J 31/00
(52) U.S. Cl. ........................... 556/12; 556/21; 556/121; 556/122; 556/123; 556/128; 556/130; 556/135; 502/152; 502/155; 526/128; 526/308
(58) Field of Search ............................... 556/121, 122, 556/123, 128, 130, 135, 12, 21; 502/152, 155; 526/128, 308

(56) References Cited

FOREIGN PATENT DOCUMENTS

FR    WO94742197    11/1997

OTHER PUBLICATIONS

Chemical Abstracts, vol. 93, No. 8, Massacessi, M. et al. "Host–lattice effects on the electron spin resonance spectra of copper (II) complexes in duluted and undiluted forms" &J. Mol. Struct. (1980), 64, 269–76, 1980.
Plappert, Elisabeth C. et al., "Synthesis and structural Characterization of silver (I) compounds with nitrogen ligands" J. Chem. Soc., Dalton Trans. (1997) (12), 2119–2123.
Chemical Abstracts, vol. 81, No. 12, Sep. 23, 1974 Porzolt, Eva CS. et al. "Interaction of mercury (II) cyanide with ligands containing nitrogen as a donar atom" & Magy. Kem. Foly. (1974), 80(3), 1974.*
Chemical Abstracts, vol. 101, No. 20, Gampp, Harald "Investigation of solution kinetics of transition–metal complexes by EPR spectroscopy" & Inorg. Chem. (1984), 23(22), 3645–9, 1984.
Barbucci, Rolando et al; "Thermodynamic, electonic, and electron paramagnetic resonance investigation of the coordinating properties of 3–azaheptane–1,7,–diamine in aqueous solutions" J. Chem. Soc., Dalton Trans. (1976), (14) 1321–5 1976.

* cited by examiner

Primary Examiner—Porfirio Nazario-Gonzalez
(74) Attorney, Agent, or Firm—Muserlian, Lucas and Mercanti

(57) ABSTRACT

The invention relates to new compounds having an element of group 12 and having a tridentate ligand, a process for their preparation and their use in particular as a polymerization catalyst.

14 Claims, 1 Drawing Sheet

POLYMERISATION CATALYSTS

Figure 1:
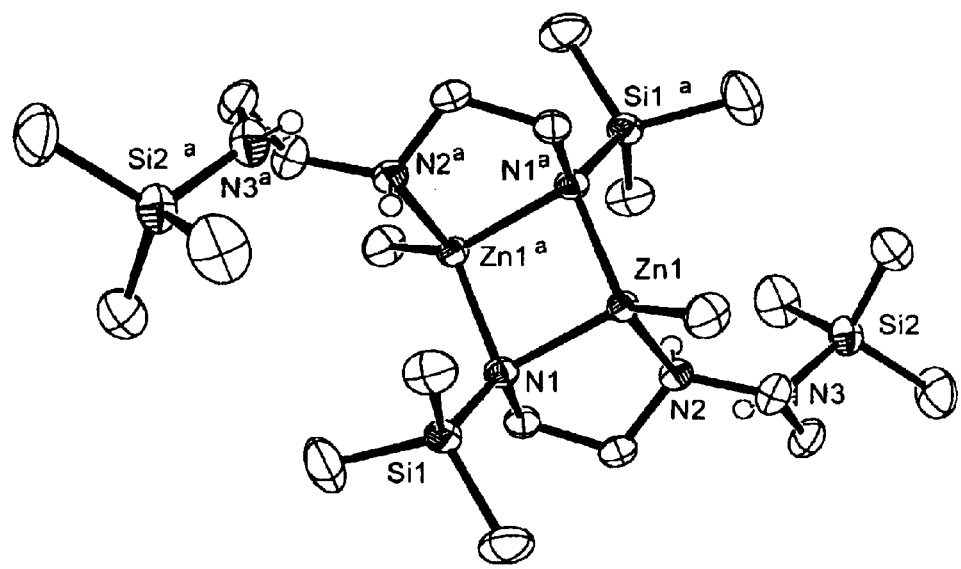

This application is a 371 of PCT FR00/01753, filed Jun. 23, 2000.

The present invention relates to new compounds having an element of group 12 and having a tridentate ligand, a process for their preparation and their use in particular as polymerization catalysts.

The use of derivatives having an element of group 12 but having porphyrin type ligands (Inoue, Acc. Chem. Res., (1996) 29, 39) as catalysts for the polymerization of heterocycles is already known.

However, it has been shown that each type of catalyst used for the polymerizations or copolymerizations, produces different polymers or copolymers respectively (Jedlinski et al., Macromolecules, (1990) 191, 2287; Munson et al., Macromolecules, (1996) 29, 8844; Montaudo et al., Macromolecules, (1996) 29, 6461). The problem is therefore to find new catalytic systems in order to obtain new polymers or copolymers, and more particularly block copolymers. The use of catalytic systems allows control of the chain formation of monomers leading to specific copolymers having the appropriate properties. This is particularly useful for biocompatible copolymers, the biodegradation of which is influenced by this chain formation.

Therefore a subject of the invention is the products of general formula I

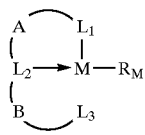

(1)

in which

M represents an element of group 12;

$R_M$ represents the hydrogen atom, a halogen atom, or an alkyl, cycloalkyl, aryl, alkoxy, cycloalkoxy, aryloxy, alkylthio, cycloalkylthio, arylthio, amino, alkylamino, dialkylamino, cycloalkylamino, di(cycloalkyl)amino, alkyl(cycloalkyl)amino, arylamino, diarylamino, alkylarylamino or (cycloalkyl)arylamino radical;

A and B represent, independently, a carbon chain of 2 to 4 carbon atoms, optionally substituted by one or more of the following substituted (by one or more identical or different substituents) or non-substituted alkyl, cycloalkyl or aryl radicals, in which said substituent is a halogen atom, the alkyl, nitro or cyano radical;

$L_1$ and $L_2$ represent, independently, a group of formula $-E_{15}(R_{15})-$ in which $E_{15}$ is an element of group 15 and $R_{15}$ represents the hydrogen atom; one of the following substituted (by one or more identical or different substituents) or non-substituted alkyl, cycloalkyl or aryl radicals, in which said substituent is a halogen atom, the alkyl, nitro or cyano radical; a radical of formula $-E_{14}RR'R''$ in which $E_{14}$ is an element of group 14 and R, R' and R'' represent, independently, the hydrogen atom or one of the following substituted (by one or more identical or different substituents) or non-substituted alkyl, cycloalkyl, aryl, alkoxy, cycloalkoxy, aryloxy, alkylthio, cycloalkylthio or arylthio radicals, in which said substituent is a halogen atom, the alkyl, nitro or cyano radical; or a radical of formula $-SO_2Q$ in which Q represents a halogen atom, an alkyl, haloalkyl or aryl radical optionally substituted by one or more substituents chosen from the alkyl, haloalkyl and halogen radicals.

$L_3$ indifferently represents a group of formula $-E'_{15}(R'_{15})(R''_{15})$ or $-E_{16}(R_{16})$ in which $E'_{15}$ is an element of group 15 and $E_{16}$ is an element of group 16 and $R'_{15}$, $R''_{15}$ and $R_{16}$ represent, independently, the hydrogen atom; one of the following substituted (by one or more identical or different substituents) or non-substituted alkyl, cycloalkyl or aryl radicals, in which said substituent is a halogen atom, the alkyl, nitro or cyano radical; a radical of formula $-E'_{14}TT'T''$ in which $E'_{14}$ is an element of group 14 and T, T' and T'' represent, independently, the hydrogen atom or one of the following substituted (by one or more identical or different substituents) or non-substituted alkyl, cycloalkyl, aryl, alkoxy, cycloalkoxy, aryloxy, alkylthio, cycloalkylthio or arylthio radicals, in which said substituent is a halogen atom, the alkyl, nitro or cyano radical; or a radical of formula $-SO_2Q'$ in which Q' represents a halogen atom, an alkyl, haloalkyl or aryl radical optionally substituted by one or more substituents chosen from the alkyl, haloalkyl and halogen radicals.

In the definitions indicated above, the expression halogen represents a fluorine, chlorine, bromine or iodine atom, preferably chlorine. The expression alkyl preferably represents a linear or branched alkyl radical having 1 to 6 carbon atoms and in particular an alkyl radical having 1 to 4 carbon atoms such as the methyl, ethyl, propyl, isopropyl, butyl, isobutyl, sec-butyl and tert-butyl radicals.

The term haloalkyl preferably designates radicals in which the alkyl radical is as defined above and is substituted by one or more halogen atoms as defined above such as, for example, bromoethyl, trifluoromethyl, trifluoroethyl or also pentafluoroethyl. The alkoxy radicals can correspond to radicals in which the alkyl radical is as defined above. The methoxy, ethoxy, isopropyloxy or tert-butyloxy radicals are preferred. The alkylthio radicals preferably represent radicals in which the alkyl radical is as defined above such as, for example, methylthio or ethylthio. The alkylamino and dialkylamino radicals preferably represent the radicals in which the alkyl radical is as defined above such as, for example, methylamino or dimethylamino.

The cycloalkyl radicals are chosen from saturated or unsaturated monocyclic cycloalkyls. The saturated monocyclic cycloalkyl radicals can be chosen from the radicals having 3 to 7 carbon atoms such as cyclopropyl, cyclobutyl, cyclopentyl, cyclohexyl or cycloheptyl radicals. The unsaturated cycloalkyl radicals can be chosen from cyclobutene, cyclopentene, cyclohexene, cyclopentadiene and cyclohexadiene radicals. The cycloalkoxy radicals can correspond to radicals in which the cycloalkyl radical is as defined above. The cyclopropyloxy, cyclopentyloxy or cyclohexyloxy radicals are preferred. The cycloalkylthio radicals can correspond to radicals in which the cycloalkyl radical is as defined above such as for example cyclohexylthio. The cycloalkylamino and di(cycloalkyl)amino radicals can correspond to radicals in which the cycloalkyl radical is as defined above such as for example cyclohexylamino and di(cyclohexyl)amino.

The aryl radicals can be of mono or polycyclic type. The monocyclic aryl radicals can be chosen from the phenyl radicals optionally substituted by one or more alkyl radicals, such as tolyl, xylyl, mesityl and cumenyl. The polycyclic aryl radicals can be chosen from the naphthyl, anthryl and phenanthryl radicals. The aryloxy radicals can correspond to radicals in which the aryl radical is as defined above. The phenoxy, 2,4,6-tritertiobutylphenoxy, tolyloxy or mesityloxy radicals are preferred. The arylthio radicals preferably designate the radicals in which the aryl radical is as defined above such as for example in phenylthio radicals. The arylamino and diarylamino radicals preferably designate radicals in which the aryl radical is as defined above such as, for example, phenylarnino or diphenylamino radicals.

The alkyl (cycloalkyl)amino radicals can correspond to radicals in which the alkyl and cycloalkyl radicals are as defined above such as, for example methyl(cyclohexyl)amino.

The alkyl arylamino radicals preferably designate radicals in which the alkyl and aryl radicals are as defined above such as, for example methylphenylamino. The (cycloalkyl)arylamino radicals can correspond to the radicals in which the cycloalkyl and aryl radicals are as defined above such as, for example (cyclohexyl)phenylamino.

The compounds of formula 1 can be presented in the form of a monomer or of a dimer and more particularly the compounds of formula 1 in which M represents a zinc atom generally presented in dimer form.

A more particular subject of the invention is the products of general formula I as defined above, characterized in that $R_M$ represents an alkyl radical;

A and B represent, independently, a carbon chain with 2 to 4 carbon atoms;

$L_1$ and $L_2$ represent, independently, a radical of formula -$E_{15}(R_{15})$— in which $E_{15}$ is a nitrogen or phosphorus atom and $R_{15}$, represents a hydrogen atom or a radical of formula -$E_{14}RR'R''$ in which $E_{14}$ represents a carbon or silicon atom and R, R' and R'' represent, independently, the hydrogen atom or an alkyl radical;

$L_3$ represents a radical of formula -$E'_{15}(R'_{15})(R''_{15})$ in which $E'_{15}$ is a nitrogen or phosphorus atom, and $R'_{15}$ and $R''_{15}$ represent, independently, a hydrogen atom or a radical of formula -$E'_{14}TT'T''$ in which $E'_{14}$ represents a carbon or silicon atom and T, T' and T'' represent, independently, the hydrogen atom or an alkyl radical.

Preferably, M represents a zinc atom. Preferably also, $R_M$ represents a methyl radical; A and B represent, independently, a carbon chain with 2 carbon atoms; $L_1$ and $L_2$ represent, independently, a radical of formula -$E_{15}(R_{15})$— in which $E_{15}$ is a nitrogen atom and $R_{15}$ represents a hydrogen atom, a methyl, ethyl, propyl, isopropyl radical or a radical of formula -$E_{14}RR'R''$ in which $E_{14}$ represents a silicon atom and R, R' and R'' represent, independently, the hydrogen atom or a methyl, ethyl, propyl or isopropyl radical; $L_3$ represents a radical of formula -$E'_5(R'_{15})(R''_{15})$ in which $E'_{15}$ is a nitrogen atom, and $R'_{15}$ and $R''_{15}$ represent, independently, a hydrogen atom, a methyl, ethyl, propyl, isopropyl radical or a radical of formula -$E'_{14}TT'T''$ in which $E'_{14}$ represents a silicon atom and T, T' and T'' represent, independently, the hydrogen atom or a methyl, ethyl, propyl or isopropyl radical.

More particularly, a subject of the invention is the products described hereafter in the examples, in particular the products corresponding to the following formulae:

- [Me$_3$SiN(H)CH$_2$CH$_2$N(Me)CH$_2$CH$_2$NSiMe$_3$]ZnMe;

- [Me$_3$SiN(H)CH$_2$CH$_2$N(H)CH$_2$CH$_2$NSiMe$_3$]ZnMe.

A subject of the invention is also a process for the preparation of the. products of general formula I as defined above, characterized in that a product of formula 1

(L$_1$-A-L$_2$-B-L$_3$)$^-$, Y$^+$         (I)

in which $L_1$, A, $L_2$, B and $L_3$ have the meanings indicated above and Y represents the hydrogen atom, a metal or a metallic group, is reacted with a product of formula II

MR$_M$Z         (II)

in which M and $R_M$ have the meanings indicated above and Z represents a parting group, in order to obtain a product of formula I as defined above.

The reaction of a compound of general formula I with a compound of general formula II in order to obtain a compound of general formula 1, can be carried out under an inert atmosphere such as under a freon or argon atmosphere, in an aprotic solvent, at a temperature comprised between −90 and +50° C. The compounds I thus obtained are purified by standard purification methods.

As aprotic solvent, aromatic hydrocarbons such as benzene, toluene; aliphatic hydrocarbons such as pentane, heptane, hexane, cyclohexane; ethers such as diethylether, dioxane, tetrahydrofuran, ethyltertiobutyl ether can be used.

In the Compounds I, Y represents the hydrogen atom, a metal or a metallic group. The metallic group can be a compound of formula R'''M$_1$ or R'''$_3$M$_2$ in which R''' represents a halogen atom, or indifferently, an alkyl, cycloalkyl, aryl, alkoxy, cycloalkoxy or aryloxy radical as previously defined, M$_1$ is a zinc or mercury atom or an alkaline-earth such as magnesium and M$_2$ a tin or lead atom; preferably, the metallic group is chosen from the MgBr, ZnMe, SnMe$_3$, SnBu$_3$ or PbMe$_3$ groups. The metal can be an alkali metal chosen from lithium, sodium or potassium.

In the compounds II, Z represents a parting group such as a halogen atom, an alkyl, cycloalkyl, alkoxy, aryl, aryloxy, amino, alkylamino or dialkylamino group as previously defined, or also a methanesulphonyloxy, a benzenesulphonyloxy, p-toluenesulphonyloxy group.

The starting products of formula I are known products or can be prepared from known products. For their synthesis, the following references can be mentioned: Cloke et al., J. Chem. Soc., Dalton Trans. (1995) 25; Wilkinson and Stone, Comprehensive Organometallic Chemistry (1982) vol. 1, 557.

The products of formula II are commercially available or can be manufactured by methods known to a person skilled in the art.

A subject of the invention is also the use of the products of formula 1 as defined above, as catalysts for carrying out (co)polymerization, that is to say of polymerization or copolymerization. Whilst carrying out (co)polymerization, the compounds according to the invention also play the role of chain initiator and/or of regulator.

The compounds of formula 1 are particularly useful for carrying out the polymerization of heterocycles. The heterocycles can contain one or more heteroatoms of groups 15 and/or 16, and have a size ranging from three to eight members. As an example of heterocycles corresponding to the previous formulation, epoxides, thioepoxides, cyclic esters or thioesters such as lactones, lactames and anhydrides can be mentioned.

The compounds of formula I are also particularly useful for carrying out the (co)polymerization of cyclic esters. As an example of cyclic esters, the polymer cyclic esters of lactic and/or glycolic acid can be mentioned. Random or block copolymers can be obtained depending on whether the monomers are introduced together at the start of the reaction, or sequentially during the course of the reaction.

A subject of the invention is also a process for the preparation of random or block copolymers, or polymers which consists of bringing into contact one or more monomers, a chain initiator and/or a regulator, a polymerization catalyst and optionally a polymerization solvent, said process characterized in that the chain initiator and/or chain regulator and the polymerization catalyst are represented by the same compound which is chosen from the compounds of formula (I) as defined above.

The (co)polymerization can be carried out either in solution or in supercooling. When the (co)polymerization is carried out in solution, the reaction solvent can be the (or one of the) substrate(s) used in the catalytic reaction. Solvents which do not interfere with the catalytic reaction itself, are also suitable. As an example of such solvents, saturated or aromatic hydrocarbons, ethers, aliphatic or aromatic halides can be mentioned.

The reactions are carried out at temperatures comprised between ambient temperature and approximately 250° C.; the temperature range comprised between 40 and 200° C. is most advantageous. The durations of the reactions are comprised between a few minutes and 300 hours, and preferably between 5 minutes and 72 hours.

This (co)polymerization process is particularly suitable for obtaining (co)polymers of cyclic esters, in particular the polymer cyclic esters of lactic and/or glycolic acid. The products obtained such as the biodegradable glycolic lactic copolymers, are advantageously used as a support in sustained release therapeutic compositions. The process is also particularly well suited to the polymerization of epoxides, in particular propylene oxide.

The polymers obtained are compounds which can be used for the synthesis of organic liquid crystals or also as semipermeable membranes.

The invention also relates to the polymers or copolymers which can be obtained by carrying out a process as described above.

The following examples are presented to illustrate the above procedures and should in no way be considered as limiting the scope of the invention.

EXAMPLE 1

$[Me_3SiN(H)CH_2CH_2N(H)CH_2CH_2NSiMe_3]ZnMe$
(in Dimer Form)

4.3 g (17.7 mmol) of $[(Me_3SiN(H)CH_2CH_2)_2NH]$ and 30 ml of toluene are successively introduced into a Schlenk tube equipped with a magnetic stirrer and purged under argon. The reaction mixture is cooled down to −78 C., then 8.8 ml (17.7 mmol) of a 2M solution of $ZnMe_2$ in toluene is introduced. The reaction mixture is brought to ambient temperature then left under agitation for 18 hours at ambient temperature. After evaporating the solvent, an orange oil is obtained. The desired compound is isolated in the form of colourless crystals by crystallization at −20 C. from pentane (5 ml) (yield 50%). This compound is characterized by multinuclear magnetic resonance spectroscopy and X-ray diffraction (FIG. 1 and Table 1 below).

EXAMPLE 2

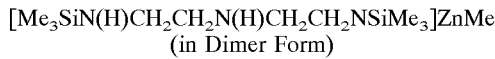
(in Dimer Form)

1.1 g (4.2 mmol) of $[(Me_3SiN(H)CH_2CH_2)_2NMe]$ and 20 ml of toluene are successively introduced into a Schlenk tube equipped with a magnetic stirrer and purged under argon. The reaction mixture is cooled down to −78 C., then 2.1 ml (4.2 mmol) of a 2M solution of $ZnMe_2$ in toluene is introduced. The reaction mixture is brought to ambient temperature then left under agitation for 3 hours at ambient temperature. After evaporating the solvent, an orange oil is obtained. The desired compound is isolated in the form of white crystals by crystallization at −20° C. from pentane (5 ml) (yield 50%). This compound is characterized by multinuclear magnetic resonance spectroscopy.

EXAMPLE 3

Preparation of a Poly(D,L-lactide)

0.045 g (0.14 mmol) of $[Me_3SiN(H)CH_2CH_2—N(H)CH_2CH_2NSiMe_3]ZnMe$ and 100 ml of toluene are successively introduced into a Schlenk tube equipped with a magnetic stirrer and purged under argon. The reaction mixture is brought to 80° C. 6.24 g (43.2 mmol) of D,L-lactide is then added. The reaction mixture is left under agitation at 80 ° C. for 42 hours. The polymer is characterized by carbon and proton NMR; the conversion of the monomer is 96%. According to a GPC analysis (Gel Permea Chromatography) using a calibration carried out from polystyrene (PS) standards polystyrene standards of masses 761 to 400000, the sample is comprised of polymers having high masses (Mw= 40400 Dalton).

EXAMPLE 4

Preparation of a Block (D,L-lactide/glycolide) Copolymer 0.15 g (0.43 mmol) of $[Me_3SiN(H)CH_2CH_2—N(Me)CH_2CH_2NSiMe_3]ZnMe$, 3.50 g (24 mmol) of D,L-lactide and 80 ml of toluene are successively introduced into a Schlenk tube equipped with a magnetic stirrer and purged under argon. The reaction mixture is left under agitation at 85 ° C. for 18 hours. Proton NMR Analysis of the allows verification that the conversion of the monomer is greater than 94%. 2.25 g (19.4 mmol) of glycolide is added over a period of 11 days to the previous solution maintained under agitation at 80° C. Analysis of an aliquot by proton NMR shows that a copolymer is formed. The ratio of the signal integrals corresponding to the polylactide part (5.20 ppm) and polyglycolide part (4.85 ppm) is 4/1. According to a GPC analysis, using a calibration carried out from PS standards of masses of 761 to 400000, this copolymer is a mixture of macromolecules having similar masses (Mw/Mn=1.63; Mw=2960 Dalton).

EXAMPLE 5

Preparation of a Random (D,L-lactide/glycolide) Copolymer 0.05 g (0.15 mmol) of $[Me_3SiN(H)CH_2CH_2—N(Me)CH_2CH_2NSiMe_3]ZnMe$, 6.66 g (45 mmol) of D,L-lactide and 1.53 g (13 mmol) of glycolide are successively introduced into a Schlenk tube equipped with a magnetic stirrer and purged under argon. The reaction mixture is heated to 180° C. for 2 hours. The polymer is characterized by proton NMR; the conversion of monomers is total. The ratio of the signal integrals corresponding to the polylactide part (5.20 ppm) and the polyglycolide part (4.85 ppm) is 4/1. According to a GPC analysis, using a calibration carried out from PS standards of masses of 761 to 400000, the sample comprises polymers with a polydispersity (Mw/Mn) of 2.27 and molecular weight (Mw) of 16271 Dalton.

EXAMPLE 6

Preparation of a Random (D,L-lactide/glycolide) Copolymer Having a Lactide/glycolide Composition Close to 70/30

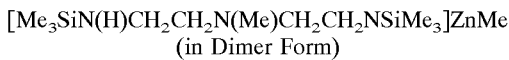, 1.98 g (13.6 mmol) of D,L-lactide and 0.68 g (5.8 mmol) of glycolide are successively introduced into a Schlenk tube equipped with a magnetic stirrer and purged under argon. The reaction mixture is left under agitation at 180° C. for 2 hours. Analysis by proton NMR allows verification that the conversion of the monomers is 98% lactide and 100% glycolide. The ratio of the signal integrals corresponding to the polylactide part (5.20 ppm) and the polyglycolide part (4.85 ppm) the composition of the copolymer to be evaluated at 65% of lactide and 35% of glycolide. According to a GPC analysis, using a calibration carried out from PS standards of masses 761 to 400000, this copolymer is a mixture of macromolecules (Mw/Mn=2.84) of high masses (Mw=34500 Dalton).

TABLE 1

Lengths of the selected bonds (in Angström) and bond angles (in degrees) for the compound of Example 1

| | | | |
|---|---|---|---|
| Zn(1)—C(1) | 1.989 (2) Å | C(5)—C(6) | 1.519 (3) Å |
| Zn(1)—N(1) | 2.086 (2) Å | C(6)—N(2) | 1.475 (3) Å |
| Zn(1)—N(2) | 2.145 (2) Å | N(2)—C(7) | 1.472 (3) Å |
| Zn(1)—N(1A) | 2.084 (2) Å | N(2)—C(7) | 1.472 (3) Å |
| N(1)—If(1) | 1.725 (2) Å | C(7)—C(8) | 1.519 (3) Å |
| N(3)—If(2) | 1.711 (2) Å | C(8)—N(3) | 1.453 (3) Å |
| N(1)—C(5) | 1.483 (3) Å | | |
| N(1)—Zn(1)—N(2) | 85.1 (1)° | Si(1)—N(1)—Zn(1) | 119.5 (1) (2)° |
| N(1)—Zn(1)—C(1) | 129.2 (1)° | Si(1)—N(1)—Zn(1A) | 120.8 (1)° |
| N(1)—Zn(1)—N(1A) | 93.7 (1)° | Si(1)—N(1)—C(5) | 112.7 (1)° |
| N(2)—Zn(1)—C(1) | 112.1 (1)° | Zn(1)—N(1)—Zn(1A) | 86.3 (1)° |
| N(2)—Zn(1)—N(1A) | 109.4 (4)° | Zn(1)—N(1)—C(5) | 106.2 (1)° |
| C(1)—Zn(1)—N(1A) | 120.1 (1)° | Zn(1A)—N(1)—C(5) | 108.0 (1)° |

What is claimed is:

1. A compound of the formula

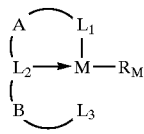
(1)

wherein

M is an element of group 12 of the Periodic Table;

$R_M$ is selected from the group consisting of hydrogen, halogen, alkyl, cycloalkyl, aryl, alkoxy, cycloalkoxy, aryloxy, alkylthio, cycloalkylthio, arylthio, amino, alkylamino, dialkylamino, cycloalkylamino, di(cycloalkyl) amino, alkyl (cycloalkyl) amino, arylamino, diarylamino, alkylarylamino and (cycloalkyl)arylamino;

and B are independently selected from the group consisting of carbon chain of 2 to 4 carbon atoms, optionally substituted by at least one member of the group consisting of substituted or non-substituted alkyl, cycloalkyl, and aryl, the substituent is selected from the group consisting of halogen, alkyl, nitro and cyano;

$L_1$ and $L_2$ are independently -$E_{15}$(R15)- in which $E_{15}$ is an element of group 15 of the Periodic Table and $R_{15}$ is selected from the group consisting of hydrogen, substituted or non-substituted alkyl, cycloalkyl and aryl, in which said substituent is selected from the group consisting of halogen, alkyl, nitro and cyano; or -$E_{14}$RR'R" in which $E_{14}$ is an element of group 14 of the Periodic Table and R, R' and R" are independently selected from the group consisting of hydrogen, substituted or non-substituted alkyl, cycloalkyl, aryl, alkoxy, cycloalkoxy, aryloxy, alkylthio, cycloalkylthio and arylthio, in which the substituents are at least one member of the group consisting of halogen, alkyl, nitro and cyano; or —$SO_2Q$ in which Q is selected from the group consisting of halogen, alkyl, haloalkyl and aryl optionally substituted by at least one substituent selected from the group consisting of alkyl, haloalkyl and halogen;

$L_3$ is -$E'_{15}$($R'_{15}$) ($R''_{15}$) or -$E_{16}$($R_{16}$) in which
$E'_{15}$ is an element of group 15 of the Periodic Table and
$E_{16}$ is an element of group 16 of the Periodic Table and
$R'_{15}$ and $R''_{15}$ are, independently, selected from the group consisting of hydrogen, substituted or non-substituted alkyl, cycloalkyl and aryl, in which the substituents are at least one member of the group consisting of halogen, alkyl, nitro and cyano; or -$E'_{14}$TT'T" in which $E'_{14}$ is an element of group 14 of the Periodic Table and T, T' and T" are independently selected from the group consisting of hydrogen, substituted or non-substituted alkyl, cycloalkyl, aryl, alkoxy, cycloalkoxy, aryloxy, alkylthio, cycloalkylthio and arylthio, in which said substituents are at least one member of the group consisting of halogen, alkyl, nitro and cyano; or —$SO_2Q$ in which Q' is selected from the group consisting of halogen, alkyl, haloalkyl and aryl optionally substituted by at least one member of the group consisting of alkyl, haloalkyl and halogen.

2. A compound of claim 1, in the form of a monomer or a dimer.

3. A compound of claim 1 wherein $R_M$ is alkyl;

A and B are, independently, a carbon chain of 2 to 4 carbon atoms;

$L_1$ and $L_2$ are, independently, -$E_{15}$($R_{15}$)— in which $E_{15}$ is nitrogen or phosphorus and $R_{15}$ is hydrogen or -$E_{14}$RR'R" in which $E_{14}$ is carbon or silicon and R, R' and R" are, independently, hydrogen or alkyl;

$L_3$ is -$E'_{15}$($R'_{15}$) ($R''_{15}$) in which $E'_{15}$ is nitrogen or phosphorus, and $R'_{15}$ and $R''_{15}$ are, independently, hydrogen; or -$E'_{14}$TT'T" in which $E'_{14}$ is carbon or silicon atom and T, T' and T" are, independently, hydrogen or alkyl.

4. A compound of claim 1 wherein M is zinc.

5. A compound of claim 1 wherein $R_M$ is methyl;

A and B are, independently, a carbon chain of 2 carbon atoms;

$L_1$ and $L_{12}$ are, independently, -$E_{15}$($R_{15}$)— in which $E_{15}$ is nitrogen and $R_{15}$ is selected from the group consisting of hydrogen, methyl, ethyl, propyl, isopropyl and -$E_{14}RR'R''$ in which $E_{14}$ is silicon and R, R' and R'' are, independently, selected from the group consisting of hydrogen, methyl, ethyl, propyl and isopropyl;

$L_3$ is -$E'_{15}(R'_{15})(R''15)$ in which $E'_{15}$ is nitrogen, and $R'_{15}$ and $R''_{15}$ are, independently, selected from the group consisting of hydrogen, methyl, ethyl, propyl, isopropyl and -$E'TT'T''$ in which $E'_{14}$ is silicon and T, T' and T'' are, independently, selected from the group consisting of hydrogen, methyl, ethyl, propyl, and isopropyl.

6. A compound of claim 1 which is

-[Me$_3$SiN(H)CH$_2$CH$_2$N(Me)CH$_2$CH$_2$NSiNe$_3$]ZnMe; or

-[Me$_3$SiN(H)CH$_2$CH$_2$N(H)CH$_2$CH$_2$NSiMe$_3$]Zn Me.

7. A compound of claim 6 in dimer form.

8. A process for the preparation of a compound of claim 1, comprising reacting a compound of the formula

  (I)

wherein $L_1$, A, $L_2$, B and $L_3$ are defined as claim 1 and Y is hydrogen or metal or a metallic with a compound of formula

  (II)

in which M and $R_M$ are defined as in claim 1 and Z is a parting group, to obtain a compound of claim 1.

9. A process for the preparation of block or random copolymers, or polymers which comprises contacting at least one monomer, a chain initiator and/or a regulator, a polymerization catalyst and optionally a polymerization solvent, at a temperature between ambient temperature and 250° C., for a few minutes to 300 hours, wherein the chain initiator and/or the regulator and the polymerization catalyst are a compound of claim 1.

10. The process of claim 9, wherein the monomer is selected from the group consisting of epoxides, and cyclic esters.

11. In a process for the polymerization or copolymerization of heterocycles, the improvement comprising using as the polymerization catalyst a compound of claim 1.

12. The process of claim 11 wherein the heterocycle is propylene oxide.

13. In a process for the polymerization or copolymerization of cyclic esters, the improvement comprising using as the polymerization catalyst a compound of claim 1.

14. The process of claim 13 wherein the cyclic ester is that of lactic acid and/or glycolic acid.

* * * * *